(12) United States Patent
Peddi Reddy et al.

(10) Patent No.: US 9,045,473 B2
(45) Date of Patent: Jun. 2, 2015

(54) FORMS OF APIXABAN

(71) Applicant: Dr. Reddy's Laboratories Ltd., Hyderabad (IN)

(72) Inventors: Subba Reddy Peddi Reddy, Kadapa (IN); Md Arshad Alam, Kishanganj (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 0 days.

(21) Appl. No.: 13/800,472

(22) Filed: Mar. 13, 2013

(65) Prior Publication Data

US 2013/0245267 A1    Sep. 19, 2013

(30) Foreign Application Priority Data

Mar. 14, 2012  (IN) .............................. 936/CHE/2012

(51) Int. Cl.
  *C07D 471/04*   (2006.01)

(52) U.S. Cl.
  CPC .................................... *C07D 471/04* (2013.01)

(58) Field of Classification Search
  CPC ....................................................... C07D 471/04
  USPC .......................................... 514/303; 546/120
  See application file for complete search history.

(56) References Cited

U.S. PATENT DOCUMENTS

| | | | |
|---|---|---|---|
| 6,967,208 B2 * | 11/2005 | Pinto et al. .................... | 514/303 |
| 7,396,932 B2 * | 7/2008 | Shapiro et al. ................ | 546/120 |
| 2007/0203178 A1 * | 8/2007 | Malley et al. ................. | 514/303 |

* cited by examiner

*Primary Examiner* — D M Seaman
(74) *Attorney, Agent, or Firm* — Pergament Gilman & Cepeda LLP; Milagros A. Cepeda; Edward D. Pergament

(57) ABSTRACT

The present application relate to amorphous form of Apixaban useful in making pharmaceutically acceptable dosage forms, and to processes for their preparation.

10 Claims, 2 Drawing Sheets

FORMS OF APIXABAN

INTRODUCTION

Aspects of the present application relate to amorphous form of Apixaban that are useful in making pharmaceutically acceptable dosage forms, and to processes for their preparation.

The drug compound having the adopted name "apixaban" has a chemical name 1-(4-Methoxyphenyl)-7-oxo-6-[4-(2-oxopiperidin-1-yl)phenyl]-4,5,6,7-tetrahydro-1H-pyrazolo [3,4-c]pyridine-3-carboxamide, and the structure of Formula I. Apixaban is being developed by Bristol-Myers Squibb (BMS) and Pfizer for the prevention of venous thromboembolic events (VTE) in adults who have undergone elective hip or knee replacement surgery.

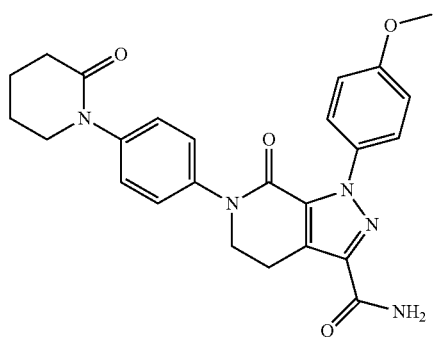

Formula I

U.S. Patent Application Publication No. 2007/0203178 A1 discloses polymorphic forms called Form DMF-5 and Form FA-2 of apixaban, and a process for preparing the same. Additionally, U.S. Pat. No. 7,396,932 discloses polymorphic forms Form H2-2 and Form N-1 of apixaban, and a process for preparing the same.

In general, polymorphism refers to the ability of a substance to exist as two or more forms that have different spatial arrangements and/or conformations of molecules in their crystal lattices. Different polymorphs may have different physical properties such as melting points, solubilities, X-ray diffraction patterns, etc. The variation in solid forms appreciably influences the pharmaceutical properties, such as bioavailability, handling properties, dissolution rate, and stability, and in turn such properties can significantly influence the processing, shelf life, and commercial acceptance of a polymorphic form. For these said reasons, regulatory authorities require drug manufacturing companies to put efforts into identifying all polymorphic forms, e.g., crystalline, amorphous, solvated, etc., of new drug substances.

The existence and possible numbers of polymorphic forms for a given compound cannot be predicted, and there are no "standard" procedures that can be used to prepare polymorphic forms of a substance. This is well-known in the art, as reported, for example, by A. Goho, "Tricky Business," *Science News*, Vol. 166(8), August 2004. However, new forms of a pharmaceutically useful compound may provide an opportunity to improve the performance characteristics of pharmaceutical products. For example, in some cases, different forms of the same drug can exhibit very different solubility and different dissolution rates. The discovery of new polymorphic forms enlarges selection of materials with which formulation scientists can design a pharmaceutically acceptable dosage form of a drug with a targeted release profile or other desired characteristics.

Hence, there remains a need for commercially viable polymorphic forms of apixaban with useful pharmaceutical properties, and processes for preparing them.

SUMMARY

In an aspect, the present application provides apixaban in an amorphous form.

In an aspect, the present application provides amorphous apixaban that can be characterized by its PXRD pattern and DSC.

In an aspect the present application provides processes for preparing an amorphous form of apixaban, embodiments comprising:
a) providing a solution of apixaban in a solvent; and
b) isolating amorphous apixaban.

In an aspect, the present application provides pharmaceutical formulation comprising an amorphous form of Apixaban, together with one or more pharmaceutically acceptable excipients.

DETAILED DESCRIPTION

Figure 1:
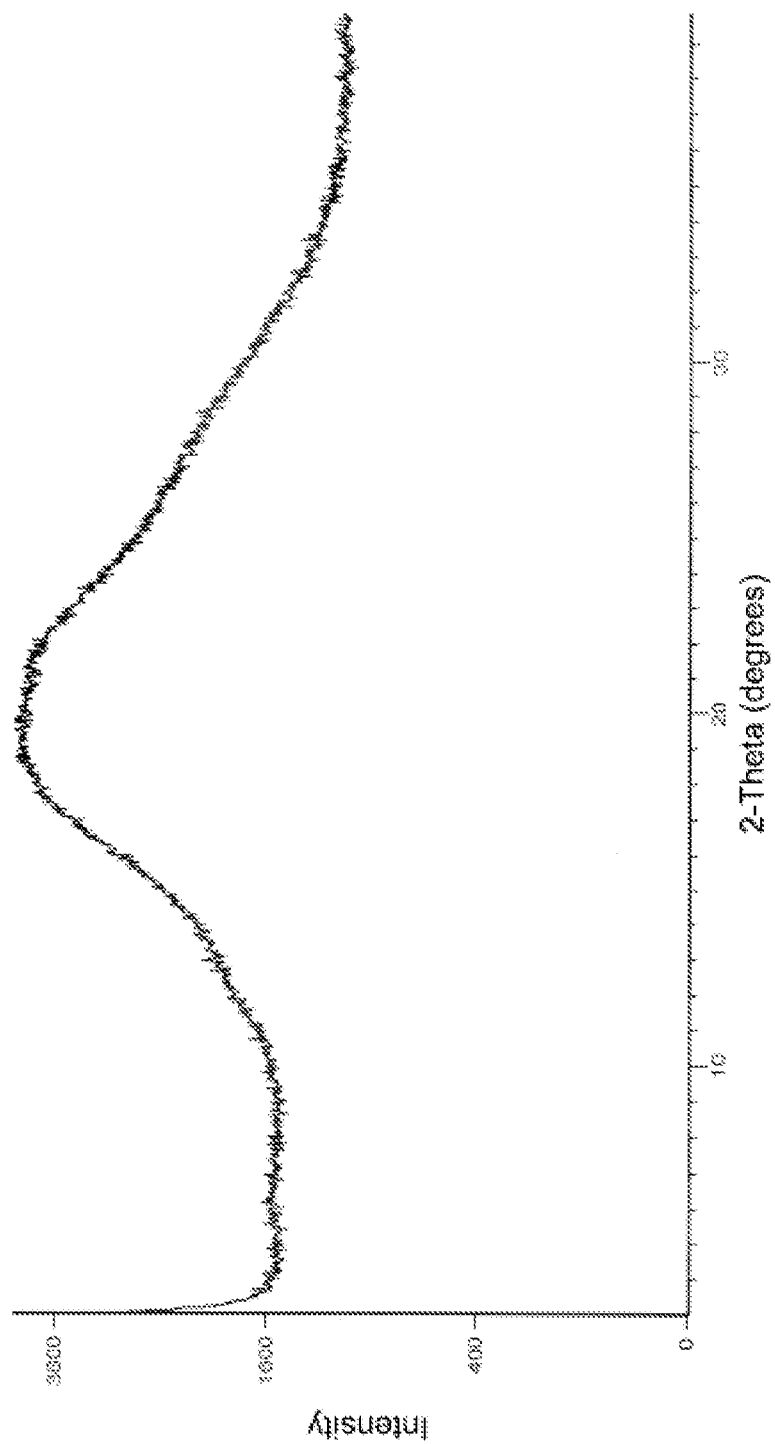
FIG. 1 is an illustration of a PXRD pattern of Apixaban prepared according to Examples 2.

In an aspect, the present application provides apixaban in amorphous form.

In an aspect the present application provides processes for preparing an amorphous form of apixaban, comprising:
a) providing a solution of apixaban in a solvent; and
b) isolating an amorphous form of apixaban.

In embodiments of step a), providing a solution of apixaban may include:
i) direct use of a reaction mixture containing apixaban that is obtained in the course of its synthesis and that comprises a suitable solvent, or by combining a solvent with the reaction mixture; or
ii) dissolving apixaban in a solvent.

In embodiments of step a), any physical form of apixaban may be utilized for providing the solution of apixaban. The dissolution temperatures may range from about 0° C. to about the reflux temperature of the solvent, or less than about 60° C., less than about 50° C., less than about 40° C., less than about 30° C., or any other suitable temperatures, as long as a clear solution of apixaban is obtained without affecting its quality. The solution may optionally be treated with carbon, flux-calcined diatomaceous earth (Hyflow), or any other suitable material to remove color, insoluble materials, improve clarity of the solution, and/or remove impurities that are adsorbable on such material. Optionally, the solution obtained may be treated to remove any insoluble particles. The insoluble particles may be removed suitably by filtration, centrifugation, decantation, or any other suitable techniques, under pressure or under reduced pressure. The solution may be filtered by passing through paper, glass fiber, cloth or other membrane material, or a bed of a clarifying agent such as Celite® or Hyflow. Depending upon the concentration and temperature of the solution and the equipment used, the filtration apparatus may optionally be preheated to avoid premature crystallization.

In embodiments of step a), suitable solvents used for providing a solution of apixaban include, but are not limited to: water; alcohols, such as methanol, ethanol, 1-propanol, 2-propanol (isopropyl alcohol), 1-butanol, 2-butanol, iso-butyl alcohol, t-butyl alcohol, and $C_1$-$C_6$ alcohols; ethers, such as diethyl ether, diisopropyl ether, methyl tertiary-butyl ether, tetrahydrofuran, 2-methyltetrahydrofuran, cyclopropylmethyl ether, dioxane, and dimethoxyethane; esters, such as methyl acetate, ethyl formate, ethyl acetate, propyl acetate, isopropyl acetate, butyl acetate, and isobutyl acetate; halogenated hydrocarbons, such as dichloromethane, 1,2-dichloroethane, trichloroethylene, perchloroethylene, 1,1,1-trichloroethane, 1,1,2-trichloroethane, chloroform, and carbon tetrachloride; ketones, such as acetone, methyl ethyl ketone, methyl isobutyl ketone, and diethyl ketone; nitriles, such as acetonitrile and propionitrile; amides, such as formamide, N,N-dimethylformamide, and N,N-dimethylacetamide; sulfoxides, such as dimethylsulfoxide; and any mixtures of two or more thereof.

In embodiments of step b), isolating an amorphous form of apixaban may be effected by removing the solvent, or by a precipitation technique. Suitable techniques which may be used for the removal of the solvent include using a rotational distillation device such as a Büchi® Rotavapor®, spray drying, thin film drying, freeze drying (lyophilization), and the like, or any other suitable techniques.

The solvent may be removed, optionally under reduced pressures, at temperatures less than about 100° C., less than about 75° C., less than about 60° C., less than about 50° C., or any other suitable temperatures.

Freeze drying (lyophilization) may be carried out by freezing a solution of apixaban at low temperatures and reducing the pressure as required to remove the solvent from the frozen solution of apixaban. Temperatures that may be required to freeze the solution, depending on the solvent chosen to make the solution of apixaban, may range from about −80° C. to about 0° C., or up to about 20° C. Temperatures that may be required to remove the solvent from the frozen solution may be less than about 20° C., less than about 0° C., less than about −20° C., less than about −40° C., less than about −60° C., less than about −80° C., or any other suitable temperatures.

In embodiments of step b), isolation may also include combining the solution of step a) with a suitable anti-solvent. Adding the solution obtained in step a) to the anti-solvent, or adding an anti-solvent to the solution obtained in step a), to effect a precipitation are both within the scope of the present application. Optionally, the combination with an anti-solvent may be carried out after concentrating the solution obtained in step a). Suitable anti-solvents that may be used include, but are not limited to: aliphatic or alicyclic hydrocarbon liquids; aromatic hydrocarbon liquids; ethers; and any mixtures thereof.

In a preferred embodiment, spray drying is employed for isolation of amorphous form of Apixaban The solid obtained from step b) may be collected using techniques such as by scraping, or by shaking the container, or other techniques specific to the equipment used. The isolated solid may be optionally further dried to afford an amorphous form of apixaban.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, at temperatures less than about 100° C., less than about 60° C., less than about 50° C., less than about 20° C., less than about 0° C., less than about −20° C., or any other suitable temperatures. The drying may be carried out for any time period required for obtaining a desired product quality, such as from about 15 minutes to 24 hours, or longer.

The dried product may be optionally subjected to a particle size reduction procedure to produce desired particle sizes and distributions. Milling or micronization may be performed before drying, or after the completion of drying of the product. Equipment that may be used for particle size reduction include, without limitation thereto, ball mills, roller mills, hammer mills, and jet mills.

In an aspect, the present application provides pharmaceutical formulations comprising an amorphous form of apixaban, together with one or more pharmaceutically acceptable excipients. Apixaban together with one or more pharmaceutically acceptable excipients of the present application may be formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization. Compositions may be presented as uncoated, film coated, sugar coated, powder coated, enteric coated, and modified release coated.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methyl celluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, or neutral surfactants; complex forming agents such as various grades of cyclodextrins and resins; and release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that are useful include, but are not limited to, film formers, plasticizers, colorants, flavoring agents, sweeteners, viscosity enhancers, preservatives, antioxidants, and the like.

In general, polymorphic forms of drug substances may be characterized by scattering techniques, such as e.g., X-ray powder diffraction patterns, by spectroscopic methods, e.g., infrared and $^{13}$C nuclear magnetic resonance spectroscopy, and by thermal techniques, e.g., differential scanning calorimetry and differential thermal analysis. Polymorphic form of the present application is characterized by the X-ray powder diffraction pattern determined in accordance with procedures that are known in the art. For a discussion of these techniques see J. Haleblian, J. Pharm. Sci. 1975 64:1269-1288, and J. Haleblian and W. McCrone, J. Pharm. Sci. 1969 58:911-929. Amorphous form of the present application can be further processed to modulate particle sizes. For example, amorphous form of the present application can be milled, to reduce average crystal size and/or to prepare a sample suitable for manipulation and formulation.

PXRD data reported herein are obtained using a PANalytical X-ray Diffractometer, with copper Kα radiation.

Amorphous form of Apixaban was further analyzed by modulated DSC (MDSC). MDSC analysis can be carried out in a DSC Q1000 instrument from TA Instruments with a ramp of 10° C./minute up to 250° C. with modulation rate of 1.59° C. per 60 s after equilibrating at 0° C. The DSC curves of the drawings have both heat flow (solid line) and reverse heat flow (dotted line) in watts/gram on y-axis and temperature in ° C. on x-axis.

DEFINITIONS

The following definitions are used in connection with the present application unless the context indicates otherwise.

The term "anti-solvent" refers to a liquid that, when combined with a solution of apixaban, reduces solubility of the apixaban in the solution, causing crystallization or precipitation in some instances spontaneously, and in other instances with additional steps, such as seeding, cooling, scratching, and/or concentrating.

Celite® is flux-calcined diatomaceous earth. Celite® is a registered trademark of World Minerals Inc.

Hyflow is flux-calcined diatomaceous earth treated with sodium carbonate. Hyflo Super Cel™ is a registered trademark of the Manville Corp.

An "aliphatic or alicyclic hydrocarbon solvent" refers to a liquid, non-aromatic, hydrocarbon, which may be linear, branched, or cyclic. It is capable of dissolving a solute to form a uniformly dispersed solution. Examples of a hydrocarbon solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, ligroin, petroleum ethers, and mixtures thereof.

"Aromatic hydrocarbon solvent" refers to a liquid, unsaturated, cyclic, hydrocarbon containing one or more rings having at least one 6-carbon ring containing three double bonds. It is capable of dissolving a solute to form a uniformly dispersed solution. Examples of an aromatic hydrocarbon solvent include, but are not limited to, benzene, toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, and mixtures thereof.

An "alcohol" is an organic compound containing a carbon bound to a hydroxyl group. "$C_1$-$C_6$ alcohols" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, phenol, glycerol, and the like An "ester" is an organic compound containing a carboxyl group —(C=O)—O— bonded to two other carbon atoms. "$C_3$-$C_6$ esters" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, and the like.

An "ether" is an organic compound containing an oxygen atom —O— bonded to two carbon atoms. Ethers include, but are not limited to, diethyl ether, diisopropyl ether, methyl t-butyl ether, glyme, diglyme, tetrahydrofuran, 1,4-dioxane, dibutyl ether, dimethylfuran, 2-methoxyethanol, 2-ethoxyethanol, anisole, $C_{3-6}$ ethers, and the like.

A "ketone" is an organic compound containing a carbonyl group —(C=O)— bonded to two other carbon atoms. "$C_3$-$C_6$ ketones" include, but are not limited to, acetone, ethyl methyl ketone, diethyl ketone, methyl isobutyl ketone, ketones, and the like.

The terms "about," "general, 'generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

A name used herein to characterize a polymorphic form for example, Form I, should not be considered limiting with respect to any other substance possessing similar or identical physical and chemical characteristics, but rather it should be understood that these designations are mere identifiers that should be interpreted according to the characterization information also presented herein.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

Certain specific aspects and embodiments of the present application will be explained in greater detail with reference to the following examples, which are provided only for purposes of illustration and should not be construed as limiting the scope of the disclosure in any manner.

EXAMPLES

Example 1

Preparation of Amorphous Apixaban

Apixaban (2 g) and dichloromethane (200 mL) were charged into a conical flask, stirred for dissolution and filtered to get a particle free solution. The solution was subjected to spray drying, to afford the title compound. Yield: 0.6 g.

Example 2

Preparation of Amorphous Apixaban

Apixaban (2.5 g) and dichloromethane (200 mL) were charged into a round bottom flask, stirred and filtered under reduced pressure to get a particle free solution. The solution was subjected to spray drying at an inlet temperature of 45° C. under a nitrogen pressure of 5 kg/cm$^2$ at a feed rate of 10%, to afford the title compound.

Figure 2:
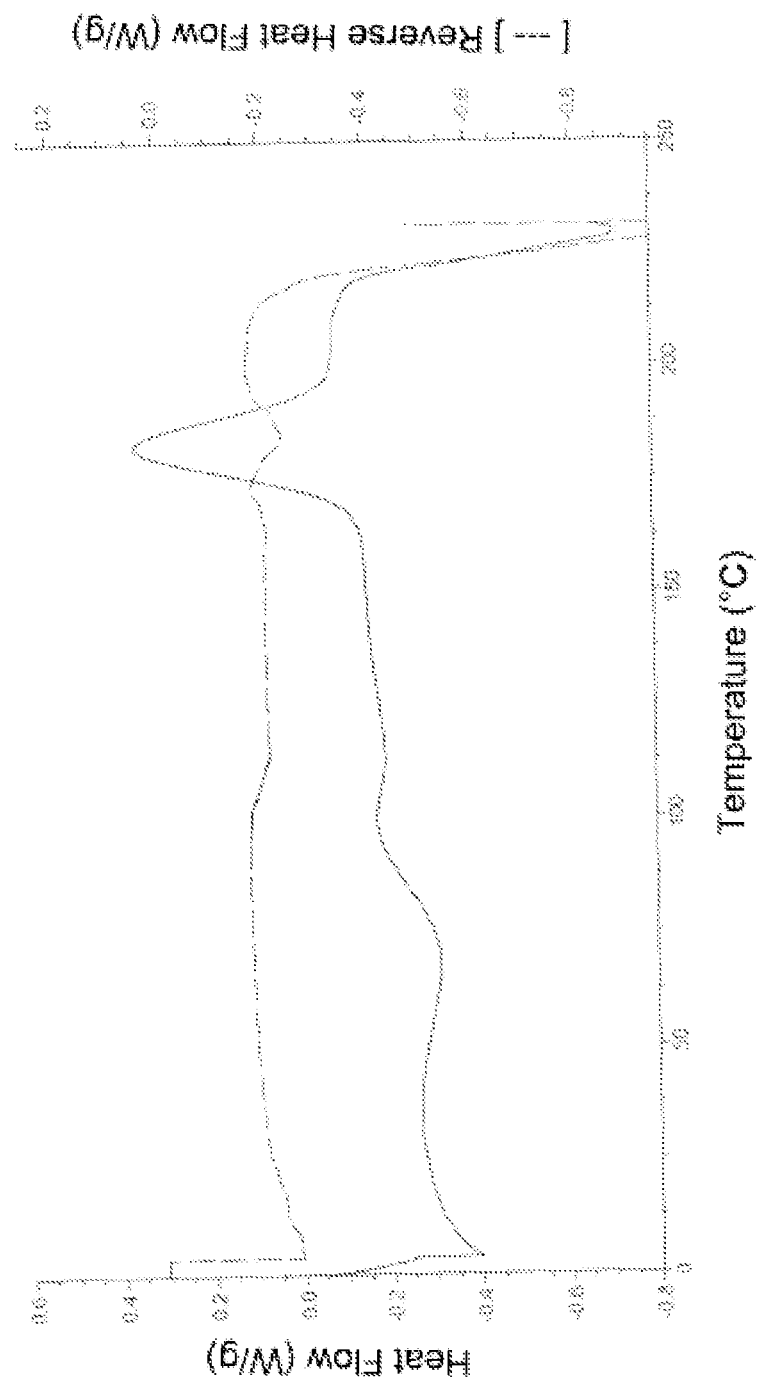
FIG. 2 is an illustration of a DSC curve of Apixaban prepared according to Example 2.

The PXRD pattern and DSC of amorphous Apixaban obtained is in accordance with FIG. 1 and FIG. 2, respectively.

Example 3

Preparation of Amorphous Apixaban

Apixaban (2 g) and methanol (400 mL) were charged into a round bottom flask, stirred. The mixture is heated to 40° C. for 10-15 minutes to make a clear solution and filtered under reduced pressure at the same temperature to get a particle free solution. The solution was subjected to spray drying at an inlet temperature of 65° C. under a nitrogen pressure of 5 kg/cm$^2$ at a feed rate of 20%, to afford the title compound.

Example 4

Preparation of Amorphous Apixaban

Apixaban (5 g) was charged in a flask followed by addition of mixture of dichloromethane (105 mL) and methanol (45 mL). The mixture was stirred at room temperature and filtered to get a particle free solution, the filter was washed with dichloromethane (17.5 mL). The solution was subjected to spray drying at an inlet temperature of 65° C. under a nitrogen pressure of 5 kg/cm$^2$ at a feed rate of 20%, to afford the desired compound. The compound obtained was subjected to drying in vacuum tray drier for 6-8 hours at 65° C.

The invention claimed is:
1. Apixaban of Formula I in solid amorphous form

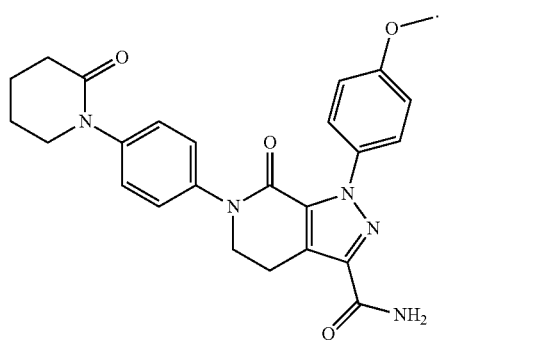

Formula I

2. A process for preparing an amorphous Apixaban according to claim 1 comprising:
   a) providing a solution of Apixaban in a solvent; and
   b) isolating amorphous Apixaban.

3. The process of claim 2 wherein suitable solvent in step a) is selected from alcohols, esters, ketones, hydrocarbons, ethers, nitriles, amides, water or mixtures thereof.

4. The process of claim 2 wherein suitable solvent in step a) is selected from alcohols and hydrocarbons.

5. The process of claim 2 wherein suitable solvent is a mixture of dichloromethane and methanol.

6. The process of claim 2 wherein in step b) the isolation is affected by evaporation, freeze drying, spray drying, lyophilization, by addition of suitable anti-solvent or any combination thereof.

7. The process of claim 2 optionally involves an additional step of drying the isolated Apixaban.

8. The process of claim 7 wherein drying is done at the temperature range 40° C. to 100° C.

9. The process of claim 7 wherein drying is performed at 60° C.

10. The process of claim 7 wherein drying is performed for 5-20 hours under vacuum.

* * * * *